(12) United States Patent
Kusunoki et al.

(10) Patent No.: US 8,993,794 B2
(45) Date of Patent: Mar. 31, 2015

(54) METHOD FOR PREPARING A POLYORGANOSILOXANE

(71) Applicant: Shin-Etsu Chemical Co., Ltd., Tokyo (JP)

(72) Inventors: Takayuki Kusunoki, Annaka (JP); Tsutomu Kashiwagi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 15 days.

(21) Appl. No.: 14/021,461

(22) Filed: Sep. 9, 2013

(65) Prior Publication Data

US 2014/0073808 A1    Mar. 13, 2014

(30) Foreign Application Priority Data

Sep. 12, 2012   (JP) ................................. 2012-200887

(51) Int. Cl.
*C07F 7/18* (2006.01)
*C08G 77/08* (2006.01)

(52) U.S. Cl.
CPC ................ *C07F 7/188* (2013.01); *C08G 77/08* (2013.01)
USPC .......................................... 556/462; 556/458

(58) Field of Classification Search
USPC ................................................ 556/458, 462
See application file for complete search history.

(56) References Cited

U.S. PATENT DOCUMENTS

| | | | |
|---|---|---|---|
| 5,109,093 A | 4/1992 | Rees et al. | |
| 6,613,440 B2 * | 9/2003 | Hara et al. | 428/447 |
| 2004/0106761 A1 | 6/2004 | Zha et al. | |
| 2009/0088547 A1 | 4/2009 | Schamschurin et al. | |

FOREIGN PATENT DOCUMENTS

| | | |
|---|---|---|
| JP | A 2-235933 | 9/1990 |
| JP | A 3-197486 | 8/1991 |
| JP | A 2006-508216 | 3/2006 |
| JP | A 2010-506982 | 3/2010 |

\* cited by examiner

*Primary Examiner* — Sudhakar Katakam
*Assistant Examiner* — Pancham Bakshi
(74) *Attorney, Agent, or Firm* — Oliff PLC

(57) ABSTRACT

A method for preparing a polyorganosiloxane, wherein the method includes a step of subjecting at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms, to a condensation reaction in the presence of a catalyst, wherein the catalyst is one obtained by surface treating at least one selected from the group consisting of hydroxides of elements in Group II of the periodic table, hydrates of hydroxides of elements in Group II of the periodic table and oxides of elements in Group II of the periodic table with a silane coupling agent.

11 Claims, No Drawings

METHOD FOR PREPARING A POLYORGANOSILOXANE

CROSS REFERENCE

This application claims the benefits of Japanese Patent application No. 2012-200887 filed on Sep. 12, 2012, the contents of which are hereby incorporated by reference.

FIELD OF THE INVENTION

The present invention relates to a method for preparing a polyorganosiloxane, specifically relates to a method for preparing a polyorganosiloxane by subjecting one or more organic silicon compounds having a silanol group, i.e., —SiOH, and/or an alkokysilyl group, i.e., —SiOR, to a condensation reaction between each other.

BACKGROUND OF THE INVENTION

In recent years, a polyorganosiloxane has attracted attentions as a material having good light permeability, good heat resistance, low gas permeability and good chemical stability. Polyorganosiloxanes having various properties are provided by changing a type of siloxane monomers, composition of raw materials and reaction conditions in the production process. On account of this, polyorganosiloxanes have been put to practical use in the various fields.

The organopolysiloxane is generally prepared by hydrolysis and condensation reaction which are caused by contacting a chlorosilane and/or alkoxysilane with a stoichiometric amount of water in an organic solvent and in the presence of an acid or base catalyst. However, in this method, a significant amount of silanol groups remains often in the obtained polyorganosiloxane and react between each other in storage to increase the viscosity to cause a problem in storage stability. Further, the unstable silanol group remaining in the polymer may cause cracks and decrease of the adhesiveness in a long-term use. Further, because the polyorganosiloxane obtained from the hydrolysis and condensation reaction has a random structure, polyorganosiloxane with desired properties is not always obtained.

Examples of the other methods for preparing a polyorganosiloxane include a method where an organic silicon compound having a silanol group, i.e., —SiOH, condensation reacts with each other in the presence of catalyst; a method where an organic silicon compound having a silanol group, i.e., —SiOH, condensation reacts with an organic silicon compound having an alkoxysilyl group, i.e., —SiOR, in the presence of catalyst; and a method where an organic silicon compound having a alkoxysilyl group, i.e., —SiOR, condensation reacts with each other in the presence of catalyst, wherein R represents an alkyl group or an alkokyalkyl group. In the aforesaid condensation reactions, an amount of a silanol group remaining in the polyoraganosiloxane obtained is small. However, these methods need chemically fierce catalysts to cause condensation reaction, for instance, strong acids such as sulfuric acid and hydrochloric acid; strong bases such as sodium hydroxide, potassium hydroxide and tetramethylammonium hydroxide; and Lewis acids. When the aforesaid catalysts are used, siloxane bonds (Si—O—Si) are cut to cause rearrangement during the reaction and, therefore, the polyorganosiloxane obtained has a random structure.

Japanese Patent Application Laid-Open No. H02-235933 describes that a borate or phosphate of sodium or potassium is used as a catalyst and a silanol-containing siloxanes is subjected to a condensation reaction in the presence of the catalyst to prepare an organosilicone condensate. Japanese Patent Application Laid-Open No. H03-197486 describes that silanol-containing siloxanes is subjected to a condensation reaction in the presence of a catalyst selected from the group consisting hydroxide, chloride, oxide and basic metal salt of an alkali metal or alkaline-earth metal to prepare a polyorganosiloxane. Japanese National Phase Publication No. 2006-508216 describes that hydroxide of magnesium or calcium can work as a catalyst in condition of the presence of a protonic solvent to promote a condensation reaction between a silanol-containing siloxane and an alkoxysilane. Japanese National Phase Publication No. 2010-506982 describes that a silicon containing compound having a silanol group and/or an alkoxysilyl group reacts in the presence of a catalyst selected from the group consisting of strontium oxide, barium oxide, strontium hydroxide, barium hydroxide and a mixture thereof to prepare an organosilicone condensate.

In the methods described in the afore-mentioned patent literatures, rearrangement of the polyorganosiloxane chain is minimized and, thus, a polyorganosiloxane having a controlled structure is obtained. Further, these methods have an advantage that the catalyst can be easily separated from the obtained polyorganosiloxane by filtration because these catalysts are solid. These advantages are favorable particularly in fields where accurate control on materials is required and no remaining impurity is tolerable, for instance, the fields of optical materials, electronic materials and medical materials.

PRIOR LITERATURES

Patent Literatures

[Patent Literature 1] Japanese Patent Application Laid-Open No. H02-235933
[Patent Literature 2] Japanese Patent Application Laid-Open No. H03-197486
[Patent Literature 3] Japanese National Phase Publication No. 2006-508216
[Patent Literature 4] Japanese National Phase Publication No. 2010-506982

SUMMARY OF THE INVENTION

However, the methods described in the afore-mentioned patent literatures 1 to 4 are not sufficient in terms of reaction rates yet. When an organosiloxane subjected to a reaction is sensitive to a temperature, a higher reaction rate or a more active catalyst are desirable, and a lower reaction temperature and shorter reaction time are needed. Further, a higher reaction rate is important in view of reduced production costs, for instance, by shortening a manufacturing time and reducing an amount of catalyst. Therefore, development of a catalyst system having higher activity is desired.

One object of the present invention is to provide a catalyst which has a high activity and can make a reaction time shorter in a method for preparing a polyorganosiloxane, which method comprises a step of subjecting at least one organic silicon compound having a silanol group (—SiOH) and/or an alkoxy silyl group (—SiOR). Additionally, another object of the present invention is to provide a method for preparing a polyorganosiloxane using the aforesaid catalyst.

To solve the aforesaid problems, the present inventors have made research and found that a catalyst is obtained by surface treating at least one selected from the group consisting of hydroxides of elements in Group II of the periodic table, hydrates of hydroxides of elements in Group II of the periodic table and oxides of elements in Group II of the periodic table with a silane coupling agent, and is used in the process of preparing a polyorganosilxane to make a condensation reaction time shorter without increasing an amount of impurities remaining in a product obtained.

Thus, the present invention is a method for preparing a polyorganosiloxane, wherein the method comprises a step of subjecting at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms, to a condensation reaction in the presence of a catalyst (C), characterized in that the catalyst (C) is one obtained by surface treating at least one (C1) selected from the group consisting of hydroxides of elements in Group II of the periodic table, hydrates of hydroxides of elements in Group II of the periodic table and oxides of elements in Group II of the periodic table with a silane coupling agent (C2).

The present invention can make a condensation reaction time shorter and provide a desired polyorganosiloxane effectively for preparing a polyorganosiloxane which comprises a step of subjecting at least one organic silicon compound having a silanol group and/or an alkoxy silyl group. Further, an amount of impurities remaining in a product obtained in the present method is less, so that the present method is particularly advantageous in fields where accurate control on materials is required and no remaining impurity is tolerable, for instance, the fields of optical materials, electronic materials and medical materials.

DETAILED DESCRIPTION OF THE INVENTION

The present invention will be described below in detail.

The present invention is characterized in that the catalyst (C) used in the condensation reaction is one obtained by surface treating at least one (C1) selected from the group consisting of hydroxides of elements in Group II of the periodic table, hydrates of hydroxides of elements in Group II of the periodic table and oxides of elements in Group II of the periodic table with a silane coupling agent (C2). The catalyst (C) will be explained below in detail.

The component (C1) is at least one selected from the group consisting of hydroxides of elements in Group II of the periodic table, hydrates of hydroxides of elements in Group II of the periodic table and oxides of elements in Group II of the periodic table (hereinafter these are referred to "compounds of Group II elements"). The compounds of Group II elements may be any compound which has a catalyst function to conduct a condensation reaction of an organic silicon compound having a silanol group (—SiOH) and/or a alkoxysilyl group (—SiOR). Examples of the compounds of Group II elements include radium hydroxide, barium hydroxide, strontium hydroxide, calcium hydroxide, magnesium hydroxide, beryllium hydroxide, barium hydroxide octahydrate, barium hydroxide monohydrate, strontium hydroxide octahydrate, barium oxide, strontium oxide, calcium oxide, magnesium oxide and beryllium oxide. Among these, barium hydroxide octahydrate, barium hydroxide monohydrate, barium hydroxide, barium oxide, calcium hydroxide, strontium hydroxide and strontium hydroxide octahydrate are preferred. Particularly, barium hydroxide octahydrate and strontium hydroxide octahydrate are preferred.

The present invention is characterized by the use of a catalyst obtained by surface treating the afore-mentioned compounds of Group II elements (C1) with a silane coupling agent (C2). On account of the surface treatment of the compounds of Group II elements with a silane coupling agent, aggregation of the catalyst is inhibited. Therefore, a catalyst can disperse homogeneously in a reaction system to maintain an effective surface area, so that a condensation reaction rate is made higher. That is, high activation of a catalyst is attained.

As the silane coupling agent (C2), any known silane coupling agent may be used. Particularly, in view of the dispersibility of the catalyst, a preferred silane coupling agent has a chemical structure similar to an organic silicon compound which causes a condensation reaction, particularly similar to an organic silicon compound having an alkoxy group. Examples of the silane coupling agent include trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyldimethoxysilane, 3-glicydyloxypropyltrimethoxysilane, 3-methacryloxypropyltrimethoxysilane, 3-aminopropyltrimethoxysilane, 3-mercaptpropyltrimethoxysilane, 3-chloropropyltrimethoxysilane, 1,1,3,3,5,5-hexamethoxy-1,3,5-trimethyltrisiloxane, 1,1,5,5-tetramethoxy-1,3,5-trimethyltrisiloxane-3-ol, dimethyldimethoxysilane, dimethyldiethoxysilane, phenylmethyldimethoxysilane, diphenyldimethoxysilane, distyryldimethoxysilane, dipentafluorophenyldimethoxysilane and hexamethyldisilazane. Among these, vinyltrimethoxysilane, methyltrimethoxysilane and 3-glicydyloxypropyltrimethoxysilane are preferred.

The present method may include a step of surface treating the compound of Group II elements (C1) with the silane coupling agent (C2) before the condensation reaction. The surface treatment of the compound of Group II elements (C1) with the silane coupling agent (C2) may be conducted in a conventional manner. For instance, a wet process and a dry process are utilizable. A mixing ratio of the compound of Group II elements (C1) to the silane coupling agent (C2) is not limited to particular one, but preferably the amount of the silane coupling agent (C2) is 0.001 to 100 parts by mass, more preferably 0.01 to 10 parts by mass, relative to 100 parts by mass of the compound of Group II elements (C1), so as not to damage the catalyst activity. Besides, the compound of Group II elements may be surface treated with the silane coupling agent off site. The catalyst may be a commercialized product.

An amount of the catalyst used in the present method is such that a molar amount of the compound (C1), as the compound before surface treatment with the silane coupling agent, is 0.0001 to 20 mol %, preferably 0.01 to 10 mol %, more preferably 0.1 to 1.0 mol %, relative to a total molar amount of the organic silicone compound to be subjected to a condensation reaction. When the amount of the component (C1) is in the afore-mentioned range, a sufficient catalyst effect for the condensation reaction is attained. Further, in a step of removing the catalyst by filtration after the condensation reaction, a desired condensate is recovered effectively without clogging of a filter.

The present invention provides a method for preparing a polyorganosilxane which comprises a step of subjecting at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms.

In a first embodiment of the present method, the organic silicon compound comprises
(A) at least one organic silicon compound having at least one silanol group in the molecule and
(B1) at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms.

In the second embodiment of the present method, the organic silicon compound comprises (B2) one or more organic silicon compounds having at least one —OX' group bonding to a silicon atom in the molecule, wherein X' is an alkyl group having 1 to 10 carbon atoms or an alkoxyalkyl group having 2 to 10 carbon atoms.

In the third embodiment of the present method, the organic silicon compound comprises one or more organic silicon compounds having at least one silanol group and at least one —OX' group bonding to a silicon atom in the molecule, wherein X' is an alkyl group having 1 to 10 carbon atoms or an alkoxyalkyl group having 2 to 10 carbon atoms.

Each embodiment is explained below in detail.

First Embodiment

In the first embodiment of the present invention, the component (A) is at least one organic silicon compound having at least one silanol group in the molecule and the component (B1) is at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms. The organic silicon compound may be a monomer, dimer, origomer or polymer. Further, when the organic silicon compound is an oligomer or a polymer, its structure may be linear, branched or linear with a branched part. Particularly, a linear structure is preferred. In a case where a condensate having a high molecular weight is desired, it is preferable that the polyorganosiloxane has two or more silanol or —OX groups in each molecule. Besides, when X in the component (B1) is a hydrogen atom, the component (A) may be same as the component (B).

The component (A) may be represented by the following general formula (1).

(R$^1_a$SiO$_{(4-a-b)/2}$(OH)$_b$)$_n$     (1)

In the formula (1), R$^1$ is, independently of each other, a hydrogen atom or a monovalent hydrocarbon group having 1 to 18 carbon atoms, and optionally having an oxygen, halogen, nitrogen or sulfur atom, a and b are independent among the parenthesized repeating units, a is an integer of from 0 to 3 and b is an integer of from 0 to 4, provided that the total of a and b is from 0 to 4, preferably from 2 to 4. n is an integer of from 1 to 10,000, provided that the compound (A), organic silicon compound, has at least one —OH group bonding to a silicon atom in the molecule.

The component (B1) may be represented by the following general formula (2).

(R$^1_a$SiO$_{(4-a-b-c)/2}$(OH)$_b$(OR$^2$)$_c$)$_n$     (2)

In the formula (2), R$^1$ is, independently of each other, a hydrogen atom or a monovalent hydrocarbon group having 1 to 18 carbon atoms, and optionally having an oxygen, halogen, nitrogen or sulfur atom, R$^2$ is, independently of each other, an alkyl group having 1 to 10 carbon atoms or an alkoxyalkyl group having 2 to 10 carbon atoms, a, b and c are independent among the parenthesized repeating units, a is an integer of from 0 to 3, b is an integer of from 0 to 4, and c is an integer of from 0 to 4, provided that the total of a, b and c is from 0 to 4, preferably from 2 to 4. n is an integer of from 1 to 10,000, provided that the compound (B1), organic silicon compound, has at least one —OH group bonding to a silicon atom or —OR$^2$ group bonding to a silicon atom in the molecule.

In the formulas (1) and (2), R$^1$ is, independently of each other, a monovalent hydrocarbon group having 1 to 18, preferably 1 to 10 carbon atoms, and optionally having an oxygen, halogen, nitrogen or sulfur atom. Examples of R$^1$ include alkyl groups such as methyl, ethyl, propyl, butyl and octyl groups; cycloalkyl groups such as cyclopentyl and cyclohexyl groups; alkenyl groups such as vinyl and allyl groups; aryl groups such as phenyl, tolyl and naphthyl groups; and aralkyl groups such as benzyl, phenylethyl and phenylpropyl groups; and these groups where apart or the whole of their hydrogen atoms bonding to carbon atoms are replaced with a halogen atom(s), such as fluorine, bromine and chlorine atoms, or with a cyano group, such as, for instance, halogen-substituted monovalent hydrocarbon groups such as trifluoropropyl and chloropropyl groups; a cyanoalkyl groups such as a β-cyanoethyl and γ-cyanopropyl groups; 3-methacryloxypropyl group, 3-glycidyloxypropyl group, 3-glycidyloxypropylmethyl group, 3-mercaptopropyl group and 3-aminopropyl group. Among these, methyl, phenyl, vinyl and 3-glycidyloxypropyl groups are preferred.

In the aforesaid formula (2), R$^2$ is, independently of each other, an alkyl group having 1 to 10, preferably 1 to 8 carbon atoms or an alkoxyalkyl group having 2 to 10, preferably 2 to 8 carbon atoms. Examples of R$^2$ include alkyl groups such as methyl, ethyl, propyl, butyl and octyl groups; and alkoxyalkyl group such as methoxymethyl, methoxyethyl and ethoxymethyl groups. Among these, a methyl group is preferred.

In the formulas (1) and (2), n is an integer of from 1 to 10,000, preferably 1 to 1,000. As described above, the organic silicon compound represented by the formula (1) or (2) may be a monomer (i.e., n is 1), dimer (i.e., n is 2), oligomers (e.g., n is 3 to 100) or polymer (e.g., n is 100 to 10,000). In particular, a monomer (i.e., n is 1) and a dimer (i.e., n is 2) are preferred.

The component (A) is more preferably an organic silicon compound represented by the following formula (1).

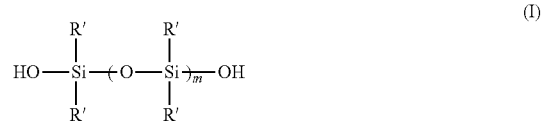

(I)

wherein R' is —OH or R$^1$, m is n−1, and R$^1$ and n are as defined above.

Examples of the organic silicon compound represented by the formula (I) includes 1,1,3,3-tetramethyldisiloxane-1,3-diol, 1,1,3,3,5,5-hexamethyltrisiloxane-1,5-diol, 1,1,3,5,5-pentamethyltrisiloxane-1,3,5-triol, 3-glycidyloxypropylmethylsilanetriol, 3-methacryloxypropylsilanetriol, 3-aminopropylsilanetriol, 3-mercaptopropylsilanetriol, 3-chloropropylsilanetriol, silicic acid, phenylmethylsilanediol, diphenylsilanediol, distyrylsilanediol and dipentafluorophenylsilanediol. Among these, diphenylsilanediol is preferred as it is easily available.

The component (81) is more preferably an organic silicon compound represented by the following formula (II) or (III).

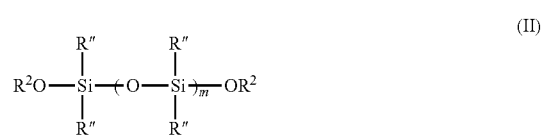

(II)

wherein R" is —OH, —OR² or R¹, preferably —OR² or R¹, m is n−1, and R¹, R² and n are as defined above.

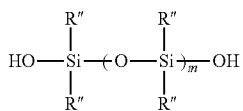

(III)

wherein R" is —OH, —OR² or R¹, preferably —OH or R¹, m is n−1, and R¹, R² and n are as defined above.

Examples of the organic silicon compound represented by the formula (II) include tetramethoxysilane, tetraethoxysilane, trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyldimethoxysilane, 3-methacryloxypropyltrimethoxysilane, 3-aminopropyltrimethoxysilane, 3-mercaptopropyltrimethoxysilane, 3-chloropropyltrimethoxysilane, 1,1,5,5-tetramethoxy-1,3,5-trimethyltrisiloxane-3-ol, dimethyldimethoxysilane, dimethyldiethoxysilane, phenylmethyldimethoxysilane, diphenyldimethoxysilane, distyryldimethoxysilane and dipentafluorophenyldimethoxysilane. Tetramethoxysilane and trimethoxysilane are preferred in view of the reactivity. Further, examples of the organic silicon compound represented by the aforesaid formula (III) includes some of the organic silicon compounds represented by the afore-mentioned formula (1), and 3-methoxy-1,3,5-trimethyltrisiloxane-1,1,5,5-tetraol.

A blend ratio of the components (A) to (B) may be decided properly, depending on a structure of a desired product, polyorganosiloxane. In particular, the number of the silanol group in the component (A) is preferably equal to the number of the —OX group in the component (B) when a condensate having high molecular weight is desired. Thus, it is preferable that the ratio of the number of the silanol group in the component (A) relative to the number of —OX group in the component (B) is 0.5 to 1.5, in particular 0.8 to 1.2, further 0.9 to 1.1.

For instance, when diphenylsilandiol is used as the component (A) and vinyl trimethoxysilane is used as the component (B), the molar ratio of the component (A) to the component (B) is preferably 3:2.

Second Embodiment

In the second embodiment of the present invention, the component (B2) is one or more organic silicon compounds having at least one —OX group bonding to a silicon atom in the molecule, wherein X' is an alkyl group having 1 to 10 carbon atoms or an alkoxyalkyl group having 2 to 10 carbon atoms. The organic silicon compound may be a monomer, dimer, origomer and polymer. Further, when the organic silicon compound is an oligomer or a polymer, its structure may be linear, branched or linear with a branched part. Particularly, a linear structure is preferred. In a case where a condensate having a high molecular weight is desired, the polyorganosiloxane preferably has two or more —OX' groups in the molecule.

The component (B2) may be represented by the following general formula (3).

(3)

In the formula (3), R¹ is, independently of each other, a hydrogen atom or a monovalent hydrocarbon group having 1 to 18, preferably 1 to 10 carbon atoms, and optionally having an oxygen, halogen, nitrogen or sulfur atom. Examples of R¹ are as described for the formulas (1) and (2) above. R² is, independently of each other, an alkyl group having 1 to 10, preferably 1 to 8 carbon atoms or an alkoxyalkyl group having 2 to 10, preferably 2 to 8 carbon atoms. Examples of R² are as described for the formula (2) above.

In the formula (3), a and c are independent among the parenthesized repeating units, a is an integer of from 0 to 3 and c is an integer of from 0 to 4, provided that the total of a and c is from 0 to 4, preferably from 2 to 4, provided that the organic silicon compound of formula (3) has at least one —OR² group in the molecule.

In the formula (3), n is an integer of from 1 to 10,000, preferably 1 to 1,000. As described above, the organic silicon compound represented by the formula (3) may be a monomer (i.e., n is 1), dimer (i.e., n is 2), oligomer (e.g., n is 3 to 100) or polymer (e.g., n is 100 to 10,000). In particular, a monomer (i.e., n is 1) and a dimer (i.e., n is 2) are preferred.

The component (B2) is more preferably an organic silicon compound represented by the following formula (IV).

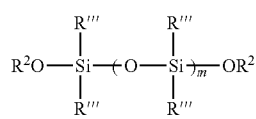

(IV)

wherein R'" is −OR² or R¹, m is n−1, and R¹, R² and n are as defined.

Examples of the organic silicon compound represented by the afore-said formula (IV) includes tetramethoxysilane, tetraethoxysilane, trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyldimethoxysilane, 3-methacryloxypropyltrimethoxysilane, 3-aminopropyltrimethoxysilane, 3-mercaptopropyltrimethoxysilane, 3-chloropropyltrimethoxysilane, dimethyldimethoxysilane, dimethyldiethoxysilane, phenylmethyldimethoxysilane, diphenyldimethoxysilane, distyryldimethoxysilane and dipentafluorophenyldimethoxysilane. Tetramethoxysilane and trimethoxysilane are preferred in view of the reactivity.

In a case when two or more kinds of the organic silicon compounds are condensation reaction with each other, a mixing ratio of the components may be desired properly, depending on structure of a desired polyorganosiloxane. In particular, the number of the —OX' group in one component is preferably equal to that in the other component. For instance, the ratio of the number of —OX' group in one organic silicon component relative to the number of —OX' group in the other organic silicon component is preferably 0.5 to 1.5, in particular 0.8 to 1.2, further 0.9 to 1.1.

Third Embodiment

The third embodiment of the present invention is a method for preparing a polyorganosiloxane comprising a step of subjecting one or more organic silicon compounds having at least one silanol group and at least one —OX' group bonding to a silicon atom in the molecule to a condensation reaction with each other, wherein X' is an alkyl group having 1 to 10 carbon atoms or an alkoxyalkyl group having 2 to 10 carbon atoms. The organic silicon compound may be a monomer, dimer, origomer or polymer. Further, when the organic silicon compound is an oligomer or a polymer, its structure may be linear, branched or linear with a branched part. Particularly, a linear structure is preferred.

The aforesaid organic silicon compound may be represented by the following general formula (4).

$$(R^1_a SiO_{(4-a-b-c)/2}(OH)_b(OR^2)_c)_n \quad (4)$$

In the formula (4), $R^1$ is, independently of each other, a hydrogen atom or a monovalent hydrocarbon group having 1 to 18 carbon atoms, and optionally having an oxygen, halogen, nitrogen or sulfur atom. Examples of $R^1$ are as described for the formulas (1) and (2) above. $R^2$ is, independently of each other, an alkyl group having 1 to 10, preferably 1 to 8 carbon atoms or an alkoxyalkyl group having 2 to 10, preferably 2 to 8 carbon atoms. Examples of $R^2$ are as described for the formula (2) above.

In the formula (4), a, b and c are independent among the parenthesized repeating units, a is an integer of from 0 to 3, b is an integer of from 0 to 4 and c is an integer of from 0 to 4, provided that the total of a, b and c is from 0 to 4, preferably from 2 to 4, provided that the organic silicon compound of formula (4) has at least one —OH group and at least one —$OR^2$ group in the molecule.

In the formula (4), n is an integer of from 1 to 10,000, preferably 1 to 1,000. As described above, the organic silicon compound represented by the formula (4) may be a monomer (i.e., n is 1), dimer (i.e., n is 2), oligomer (e.g., n is 3 to 100) or polymer (e.g., n is 100 to 10,000). In particular, a monomer (i.e., n is 1) and a dimer (i.e., n is 2) are preferred.

The aforesaid organic silicon compound is preferably represented by the following formula (v) or (VI).

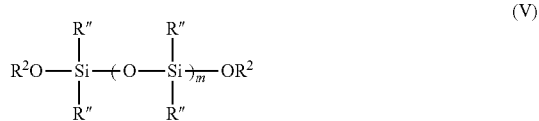

wherein R" is —OH, —$OR^2$ or $R^1$, provided that at least one of R" is —OH, m is n–1, $R^1$, $R^2$ and n are as defined above.

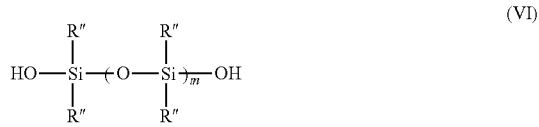

wherein R" is —OH, —$OR^2$ or $R^1$, provided that at least one of R" is —$OR^2$, m is n–1, $R^1$, $R^2$ and n are as defined above.

Examples of the organic silicon compound represented by the afore-mentioned formula (V) or (VI) include 1,1,5,5-tetramethoxy-1,3,5-trimethyltrisiloxane-3-ol, 3-methoxy-1,3,5-trimethyltrisiloxane-1,1,5,5-tetraol, 1,3-dimethoxy-1,3-dimethyldisiloxane-1,3-diol, 1,3,5-trimethoxy-1,3,5-trimethyltrisiloxane-1,5-diol, 3-methoxy-1,1,5,5-tetramethyltrisiloxane-1,3,5-triol, methoxymethylsilanediol and dimethoxysilanediol.

In a case where two or more kinds of the organic silicon compounds are a condensation reacted with each other, a mixing ratio of the components may be decided properly, depending on structure of a desired polyorganosiloxane. In particular, the total number of the silanol and —OX' groups in one component is preferably equal to that in the other component when a condensate having high molecular weight is desired. For instance, the ratio of the total number of silanol and —OX' groups in one organic silicon component relative to the total number of silanol and —OX' groups in the other organic silicon component is preferably 0.5 to 1.5, in particular 0.8 to 1.2, further preferably 0.9 to 1.1.

The condensation reaction in the present invention may be carried out in the presence of at least one solvent (D). The solvent is used to control a rate and conversion of the reaction, or used as a diluent for a condensate obtained. The solvent may be one or more selected from non-polar solvents and polar solvents. Examples of the non-polar solvents include hydrocarbons such as n-hexane, n-heptane and isooctane; aromatic hydrocarbons such as toluene and xylene. Examples of the polar solvents include water; alcohols such as methanol, ethanol and isopropanol; alcohol esters; ketons such as acetone, methylethylketone and cyclohexanone; ethers such as diethyl ether and dibutyl ether; esters such as ethyl acetate, isopropyl acetate and butyl acetate; hydrocarbon cyanides such as acetonitrile; amines; amides such as acetamide; halogenated hydrocarbons such as methylene chloride, chloroform and hexafluoromethaxylene; and sulfur-containing compounds such as dimethylsulfoxide. An amount of the solvent is not limited to particular one. Generally, the amount is such that a concentration of the organic silicon compounds subjected to the condensation reaction is 5 to 97 weight %, preferably 20 to 80 weight %. Besides, the condensation reaction in the present invention can be conducted without any solvent.

In the present condensation reaction, any other components may also be used as long as such does not obstruct the progress of the condensation reaction. For instance, a neutral surfactant may be added so as to improve dispersion of a solid catalyst. When the group represented by $R^1$ in the formulas (1) to (4) is reactive, a reaction inhibitor may be added. The afore-mentioned components may be used alone or in combination two or more of them. Further, an amount of the component may be decided properly so that the effects of the present invention are not obstructed.

The condensation reaction in the present invention may be conducted under heat conditions. A temperature is preferably 0 to 150 degrees C., more preferably 60 to 100 degrees C.

The present method preferably further comprises a step of filtering a catalyst after finishing the condensation reaction.

In the present method, the catalyst is easily removed from a reaction product in this step. In the filtration, the afore-mentioned solvent (D) may be added in order to control viscosity of the reaction mixture obtained.

Further, the present method may comprise a step of purification in order to remove an unreacted monomer from the reaction mixture by any known method such as water washing with, vacuum strip and treatment with activated carbon.

The present method makes the condensation reaction time shorter without increasing the amount of remaining impurities in the product obtained. Therefore, the desired polyorganosiloxane is provided efficiently.

EXAMPLES

The present invention will be explained below in further detail with reference to a series of the Examples and the Comparative Examples, though the present invention is in no way limited by these Examples. In the following descriptions, the term "part" refers to "part by mass".

The weight average molecular weight (Mw) described in the Examples was as determined by gel permeation chromatography, i.e., GPC, and reduced to polystyrene. Conditions in GPC were as follows.

[GPC Conditions]
Solvent: Tetrahydrofuran
Flow rate: 0.6 mL/min.
Columns; all provided by TOSCH Cop.
TSK Guardcolumn SuperH-L
TSKgel SuperH4000 (6.0 mmI.D.×15 cm×1)
TSKgel SuperH3000 (6.0 mmI.D.×15 cm×1)
TSKgel SuperH2000 (6.0 mmI.D.×15 cm×2)
Column Temperature: 40 degrees C.
Injection Volume: 20 μl of a 0.5% by weight solution in THF.
Detector: Differential refractive index detector (RI)

The components used in the Examples and Comparative Examples are as follows.

(1) Diphenylsilanediol (DPS)

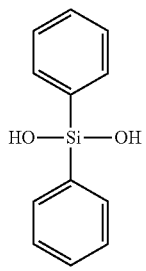

(2) 1,1,3,3-Tetramethyldisiloxane-1,3-diol(TDS)

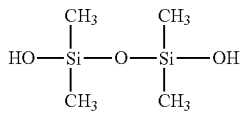

(3) Trimethoxyvinylsilane (TVS)

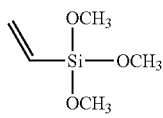

(4) Trimethoxymethylsilane (TMS)

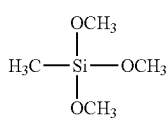

(5) 3-Glycidyloxypropyltrimethoxysilane (GTS)

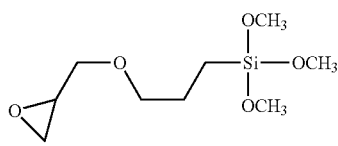 [SMILES: CO[Si](CCCOCC1CO1)(OC)OC]

Preparation Example 1

Preparation of a Catalyst 0.1 Part by mass of a silane coupling agent, trimethoxyvinyl silane or TVS, was added to 100 parts by mass of Ba(OH)$_2$.8H$_2$O and stirred well with a Henschel mixer. The mixture was dried in air at room temperature for 24 hours to obtain Ba(OH)$_2$.8H$_2$O which was surface treated with the silane coupling agent, TVS.

Preparation Example 2

Preparation of a Catalyst 0.1 part by mass of a silane coupling agent, trimethoxymethylsilane or TMS, was added to 100 parts by mass of Ba(OH)$_2$.8H$_2$O and stirred well with a Henschel mixer. The mixture was dried in air at room temperature for 24 hours to obtain Ba(OH)$_2$.8H$_2$O which was surface treated with the silane coupling agent, TMS.

Example 1

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. Ba(OH)$_2$.8H$_2$O which was surface treated with the silane coupling agent(TVS) in Preparation Example 1 was added to the mixture in an amount of Ba(OH)$_2$.8H$_2$O of 0.02 mol and, then, heated at 80 degrees C. for 4 hours to react, while removing methanol.

Example 2

259.57 g (1.2 mols) of diphenyl silane diol (DPS), 118.59 g (0.8 mol) of trimethoxyvinylsilane (TVS) and 20 wt %, based on the mixture, of xylene were mixed and heated at 80 degrees C. for 10 minutes while stirring. Ba(OH)$_2$.8H$_2$O which was surface treated with the silane coupling agent (TVS) in the Preparation Example 1 was added to the mixture in an amount of Ba(OH)$_2$.8H$_2$O of 0.02 mol and, then, heated at 80 degrees C. for 4 hours to react, while removing methanol.

Example 3

259.57 g (1.2 mols) of diphenyl silane diol (DPS), 118.59 g (0.8 mol) of trimethoxyvinylsilane (TVS) and 5 wt %, based on the mixture, of methanol were mixed and heated at 80 degrees C. for 10 minutes while stirring. Ba(OH)$_2$.8H$_2$O which was surface treated with the silane coupling agent (TVS) in the Preparation Example 1 was added to the mixture in an amount of Ba(OH)$_2$.8H$_2$O of 0.02 mol and, then, heated at 80 degrees C. for 4 hours to react, while removing methanol.

Example 4

259.57 g (1.2 mols) of diphenyl silane diol (DPS), 118.59 g (0.8 mol) of trimethoxyvinylsilane (TVS) and 3 wt %, based on the mixture, of water were mixed and heated at 80 degrees C. for 10 minutes while stirring. Ba(OH)$_2$.8H$_2$O which was surface treated with the silane coupling agent(TVS) in the Preparation Example 1 was added to the mixture in an amount of Ba(OH)$_2$.8H$_2$O of 0.02 mol and, then, heated at 80 degrees C. for 4 hours to react, while removing methanol.

Example 5

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. Ba(OH)$_2$.8H$_2$O which was surface treated with the silane coupling agent(TMS) in the Preparation Example 2 was added to the mixture in an amount of Ba(OH)$_2$.8H$_2$O of 0.02 mol and, then, heated at 80 degrees C. for 4 hours to react, while removing methanol.

Comparative Example 1

Example 1 was repeated except that Ba(OH)$_2$.8H$_2$O which had not be surface treated with a silane coupling agent was used in place of the catalyst used in Example 1.

Comparative Example 2

Example 1 was repeated except that 0.04 mol of Ba(OH)$_2$.8H$_2$O which had not be surface treated with a silane coupling agent was used in place of the catalyst used in Example 1.

In Examples 1 to 5 and Comparative Examples 1 and 2, a reaction rate and an amount of the remaining catalyst were determined according to the following manner. The results are as shown in Table 1.

[Reaction Rate]

During the reaction, the reaction mixture was observed to record a time when the reaction mixture turned from white turbidity to transparency, which means that all of the DPS monomer, which is solid powder, reacted. Subsequently, the reaction mixture was further aged. Samples of the mixture were taken at the times of one hour and four hours after starting the reaction. The weight average molecular weights (Mw) of the condensates were determined by GPC.

[Amount of the Remaining Catalyst]

After the reaction ended, the solvent was removed and, then, the catalyst was removed by filtration through a filter having pore sizes of 0.45 μm. The polyorganosiloxane obtained was dissolved in the same amount of xylene to prepare a sample solution. Ion-exchanged water was added to the sample solution in an amount of 10 times the weight of the sample solution and shaken to extract the catalyst remaining in the sample solution into water. The water extract was subjected to atomic absorption analysis to determine the amount of the catalyst remaining in the polyorganosiloxane.

Preparation Example 3

Preparation of a Catalyst 0.1 part by mass of a silane coupling agent, trimethoxyvinyl silane, TVS, was added to 100 parts by mass of Ba(OH)$_2$.H$_2$O and stirred well with a Henschel mixer. The mixture was dried in air at room temperature for 24 hours to obtain Ba(OH)$_2$—H$_2$O which was surface treated with the silane coupling agent, TVS.

Example 6

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. Ba(OH)$_2$.H$_2$O which was surface treated with the silane coupling agent (TVS) in the Preparation Example 3 was added to the mixture in an amount of Ba(OH)$_2$.H$_2$O of 0.02 mol and, then, heated at 80 degrees C. for 4 hours to react, while removing methanol.

Comparative Example 3

Example 6 was repeated except that Ba(OH)$_2$.H$_2$O which had not be surface treated with a silane coupling agent was used in place of the catalyst used in Example 6.

Comparative Example 4

Example 6 was repeated except that 0.05 mol of Ba(OH)$_2$.H$_2$O which had not be surface treated with a silane coupling agent was used in place of the catalyst used in Example 6.

In Example 6 and Comparative Examples 3 and 4, a reaction rate and an amount of the remaining catalyst were determined according to the aforesaid manner. The results are as shown in Table 2.

TABLE 1

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 1 | Ba(OH)$_2$•8H$_2$O | TVS | 0.02 | 20 | 2582 | 3241 | 120 |
| Example 2 | | | | 33 | 2396 | 3224 | 100 |
| Example 3 | | | | 12 | 2930 | 3251 | 140 |
| Example 4 | | | | 16 | 2752 | 3245 | 180 |
| Example 5 | | TMS | | 25 | 2499 | 3238 | 110 |
| Com. Ex. 1 | | — | 0.02 | 56 | 1909 | 3211 | 190 |
| Com. Ex. 2 | | — | 0.04 | 29 | 2420 | 3228 | 360 |

TABLE 2

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 6 | Ba(OH)$_2$•H$_2$O | TVS | 0.02 | 34 | 1818 | 2289 | 100 |
| Com. Ex. 3 | | — | 0.02 | 79 | 1556 | 2176 | 140 |
| Com. Ex. 4 | | — | 0.05 | 39 | 1788 | 2194 | 380 |

Preparation Example 4

Preparation of a Catalyst 0.1 part by mass of a silane coupling agent, trimethoxyvinyl silane, TVS, was added to 100 parts by mass of Ba(OH)$_2$ and stirred well with a Henschel mixer. The mixture was dried in air at room temperature for 24 hours to obtain Ba(OH)$_2$ which was surface treated with the silane coupling agent, TVS.

Example 7

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. Ba(OH)$_2$ which was surface treated with the silane coupling agent (TVS) in the Preparation Example 4 was added to the mixture in an amount of Ba(OH)$_2$ of 0.02 mol and, then, heated at 80 degrees C. for 4 hours to react, while removing methanol.

Comparative Example 5

Example 7 was repeated except that Ba(OH)$_2$ which had not be surface treated with a silane coupling agent was used in place of the catalyst used in Example 7.

In Example 7 and Comparative Example 5, a reaction rate and an amount of the remaining catalyst were determined according to the aforesaid manner. The results are as shown in Table 3.

TABLE 3

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 7 | Ba(OH)$_2$ | TVS | 0.02 | 53 | 1452 | 1880 | 90 |
| Com. Ex. 5 | | — | 0.02 | 106 | 1226 | 1796 | 120 |

Preparation Example 5

Preparation of a Catalyst 0.1 part by mass of a silane coupling agent, trimethoxyvinyl silane, TVS, was added to 100 parts by mass of BaO and stirred well with a Henschel mixer. The mixture was dried in air at room temperature for 24 hours to obtain BaO which was surface treated with the silane coupling agent, TVS.

Example 8

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. BaO which was surface treated with the silane coupling agent (TVS) in the Preparation Example 5 was added to the mixture in an amount of BaO of 0.02 mol and, then, heated at 80 degrees C. for 4 hours to react, while removing methanol.

Comparative Example 6

Example 8 was repeated except that BaO which had not be surface treated with a silane coupling agent was used in place of the catalyst used in Example 8.

In Example 8 and Comparative Example 6, a reaction rate and an amount of the remaining catalyst were determined according to the aforesaid manner. The results are as shown in Table 4.

TABLE 4

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 8 | BaO | TVS | 0.02 | 382 | 1068 | 1609 | 70 |
| Com. Ex. 6 | | — | 0.02 | 597 | 938 | 1479 | 90 |

Preparation Example 6

Preparation of a Catalyst 0.1 part by mass of a silane coupling agent, trimethoxyvinyl silane, TVS, was added to 100 parts by mass of $Ca(OH)_2$ and stirred well with a Henschel mixer. The mixture was dried in air at room temperature for 24 hours to obtain $Ca(OH)_2$ which was surface treated with the silane coupling agent, TVS.

Preparation Example 7

Preparation of a Catalyst 0.1 part by mass of a silane coupling agent, trimethoxymethyl silane, TMS, was added to 100 parts by mass of $Ca(OH)_2$ and stirred well with a Henschel mixer. The mixture was dried in air at room temperature for 24 hours to obtain $Ca(OH)_2$ which was surface treated with the silane coupling agent, TMS.

Example 9

259.57 g (1.2 mols) of diphenyl silane diol (DPS), 118.59 g (0.8 mol) of trimethoxyvinylsilane (TVS) and 5 wt %, based on the mixture, of methanol were mixed and heated at 80 degrees C. for 10 minutes with stirring. $Ca(OH)_2$ which was surface treated with the silane coupling agent (TVS) in the Preparation Example 6 was added to the mixture in an amount of $Ca(OH)_2$ of 0.02 mol and, then, heated at 80 degrees C. for 4 hours to react, while removing methanol.

Example 10

259.57 g (1.2 mols) of diphenyl silane diol (DPS), 118.59 g (0.8 mol) of trimethoxyvinylsilane (TVS) and 5 wt %, based on the mixture, of methanol were mixed and heated at 80 degrees C. for 10 minutes with stirring. $Ca(OH)_2$ which was surface treated with the silane coupling agent (TMS) in the Preparation Example 7 was added to the mixture in an amount of $Ca(OH)_2$ of 0.02 mol and, then, heated at 80 degrees C. for 4 hours to react, while removing methanol.

Comparative Example 7

Example 9 was repeated except that $Ca(OH)_2$ which had not be surface treated with a silane coupling agent was used in place of the catalyst used in Example 9.

In Examples 9 and 10 and Comparative Example 7, a reaction rate and an amount of the remaining catalyst were determined according to the aforesaid manner. The results are as shown in Table 5.

TABLE 5

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 9 | $Ca(OH)_2$ | TVS | 0.02 | 151 | 1588 | 1763 | 20 |
| Example 10 | | TMS | 0.02 | 168 | 1532 | 1693 | 20 |
| Com. Ex. 7 | | — | 0.02 | 244 | 1470 | 1609 | 40 |

Preparation Example 8

Preparation of a Catalyst 0.1 part by mass of a silane coupling agent, trimethoxyvinyl silane, TVS, was added to 100 parts by mass of $Sr(OH)_2 \cdot 8H_2O$ and stirred well with a Henschel mixer. The mixture was dried in air at room temperature for 24 hours to obtain $Sr(OH)_2 \cdot 8H_2O$ which was surface treated with the silane coupling agent, TVS.

Example 11

259.57 g (1.2 mols) of diphenyl silane diol (DPS) and 118.59 g (0.8 mol) of trimethoxyvinylsilane (TVS) were mixed and heated at 80 degrees C. for 10 minutes with stirring. $Sr(OH)_2 \cdot 8H_2O$ which was surface treated with the silane coupling agent(TVS) in the Preparation Example 8 was added to the mixture in an amount of $Sr(OH)_2 \cdot 8H_2O$ of 0.02 mol and, then, heated at 80 degrees C. for 4 hours to react, while removing methanol.

Comparative Example 8

Example 11 was repeated except that $Sr(OH)_2 \cdot 8H_2O$ which had not be surface treated with a silane coupling agent was used in place of the catalyst used in Example 11.

Comparative Example 9

Example 11 was repeated except that 0.05 mol of $Sr(OH)_2 \cdot 8H_2O$ which had not been surface treated with a silane coupling agent in place of the catalyst used in Example 11.

In Example 11 and Comparative Examples 8 and 9, a reaction rate and an amount of the remaining catalyst were determined according to the aforesaid manner. The results are as shown in Table 6.

TABLE 6

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 11 | Sr(OH)$_2$·8H$_2$O | TVS | 0.02 | 75 | 1290 | 1771 | 70 |
| Com. Ex. 8 | | — | 0.02 | 112 | 1159 | 1631 | 110 |
| Com. Ex. 9 | | — | 0.05 | 70 | 1310 | 1805 | 290 |

Preparation Example 9

Preparation of a Catalyst 0.1 part by mass of a silane coupling agent, trimethoxyvinyl silane, TVS, was added to 100 parts by mass of Sr(OH)$_2$ and stirred well with a Henschel mixer. The mixture was dried in air at room temperature for 24 hours to obtain Sr(OH)$_2$ which was surface treated with the silane coupling agent, TVS.

Example 12

259.57 g (1.2 mols) of diphenyl silane dial (DPS) and 118.59 g (0.8 mol) of trimethoxyvinylsilane (TVS) were mixed and heated at 80 degrees C. for 10 minutes with stirring. Sr(OH)$_2$ which was surface treated with the silane coupling agent (TVS) in the Preparation Example 9 was added to the mixture in an amount of Sr(OH)$_2$ of 0.02 mol and, then, heated at 80 degrees C. for 4 hours to react, while removing methanol.

Comparative Example 10

Example 12 was repeated except that Sr(OH)$_2$ which had not be surface treated with a silane coupling agent was used in place of the catalyst used in Example 12.

Comparative Example 11

Example 12 was repeated except that 0.06 mol of Sr(OH)$_2$ which had not be surface treated with a silane coupling agent was used in place of the catalyst used in Example 12.

In Example 12 and Comparative Examples 10 and 11, a reaction rate and an amount of the remaining catalyst were determined according to the aforesaid manner. The results are as shown in Table 7.

Preparation Example 10

Preparation of a Catalyst 0.1 part by mass of a silane coupling agent, 3-glycydyloxypropyltrimethoxysilane, GTS, was added to 100 parts by mass of Ba(OH)$_2$.8H$_2$O and stirred well with a Henschel mixer. The mixture was dried in air at room temperature for 24 hours to obtain Ba(OH)$_2$.8H$_2$O which was surface treated with the silane coupling agent, GTS.

Example 13

259.57 g (1.2 mols) of diphenyl silane diol (DPS) and 189.07 g (0.8 mol) of 3-glycydyloxypropyltrimethoxysilane (GTS) were mixed and heated at 80 degrees C. for 10 minutes with stirring. Ba(OH)$_2$.8H$_2$O which was surface treated with the silane coupling agent(GTS) in the Preparation Example 10 was added to the mixture in an amount of Ba(OH)$_2$.8H$_2$O of 0.02 mol and, then, heated at 80 degrees C. for 4 hours to react, while removing methanol.

Comparative Example 12

Example 13 was repeated except that Ba(OH)$_2$.8H$_2$O which had not be surface treated with a silane coupling agent was used in place of the catalyst used in Example 13.

In Example 13 and Comparative Examples 12, a reaction rate and an amount of the remaining catalyst were determined according to the aforesaid manner. The results are as shown in Table 8.

TABLE 7

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 12 | Sr(OH)$_2$ | TVS | 0.02 | 449 | 989 | 1477 | 60 |
| Com. Ex. 10 | | — | 0.02 | 780 | 870 | 1353 | 100 |
| Com. Ex. 11 | | — | 0.06 | 428 | 1004 | 1496 | 340 |

TABLE 8

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 13 | Ba(OH)$_2$•8H$_2$O | GTS | 0.02 | 65 | 1548 | 1788 | 150 |
| Com. Ex. 12 | — | — | 0.02 | 113 | 1395 | 1684 | 200 |

Preparation Example 11

Preparation of a catalyst 0.1 part by mass of a silane coupling agent, 3-glycydyloxypropyltrimethoxysilane, GTS, was added to 100 parts by mass of Ba(OH)$_2$ and stirred well with a Henschel mixer. The mixture was dried in air at room temperature for 24 hours to obtain Ba(OH)$_2$ which was surface treated with the silane coupling agent, GTS.

Example 14

259.57 g (1.2 mols) of diphenyl silane diol (DPS) and 189.07 g (0.8 mol) of 3-glycydyloxypropyltrimethoxysilane (GTS) were mixed and heated at 80 degrees C. for 10 minutes with stirring. Ba(OH)$_2$ which was surface treated with the silane coupling agent (GTS) in the Preparation Example 11 was added to the mixture in an amount of Ba(OH)$_2$ of 0.02 mol and, then, heated at 80 degrees C. for 4 hours to react, while removing methanol.

Comparative Example 13

Example 14 was repeated except that Ba(OH)$_2$ which had not be surface treated with a silane coupling agent was used in place of the catalyst used in Example 19.

Comparative Example 14

Example 14 was repeated except that 0.06 mol of Ba(OH)$_2$ which had not be surface treated with a silane coupling agent was used in place of the catalyst used in Example 14.

In Example 14 and Comparative Examples 13 and 14, a reaction rate and an amount of the remaining catalyst were determined according to the aforesaid manner. The results are as shown in Table 9.

Preparation Example 12

Preparation of a Catalyst 0.1 part by mass of a silane coupling agent, 3-glycydyloxypropyltrimethoxysilane, GTS, was added to 100 parts by mass of Sr(OH)$_2$.8H$_2$O and stirred well with a Henschel mixer. The mixture was dried in air at room temperature for 24 hours to obtain Sr(OH)$_2$.8H$_2$O which was surface treated with the silane coupling agent, GTS.

Example 15

259.57 g (1.2 mols) of diphenyl silane diol (DES) and 189.07 g (0.8 mol) of 3-glycydyloxypropyltrimethoxysilane (GTS) were mixed and heated at 80 degrees C. for 10 minutes with stirring. Sr(OH)$_2$.8H$_2$O which was surface treated with the silane coupling agent (GTS) in the Preparation Example 12 was added to the mixture in an amount of Sr(OH)$_2$.8H$_2$O of 0.02 mol and, then, heated at 80 degrees C. for 4 hours to react, while removing methanol.

Comparative Example 15

Example 14 was repeated except that Sr(OH)$_2$.8H$_2$O which had not be surface treated with a silane coupling agent was used in place of the catalyst used in Example 15.

In Example 15 and Comparative Example 15, a reaction rate and an amount of the remaining catalyst were determined according to the aforesaid manner. The results are as shown in Table 10.

TABLE 9

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 14 | Ba(OH)$_2$ | GTS | 0.02 | 158 | 1370 | 1672 | 110 |
| Com. Ex. 13 | — | — | 0.02 | 247 | 1317 | 1568 | 160 |
| Com. Ex. 14 | — | — | 0.06 | 148 | 1371 | 1677 | 490 |

TABLE 10

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 15 | $Sr(OH)_2 \cdot 8H_2O$ | GTS | 0.02 | 193 | 1353 | 1626 | 90 |
| Com. Ex. 15 | | — | 0.02 | 280 | 1283 | 1505 | 120 |

Preparation Example 13

Preparation of a catalyst 0.1 part by mass of a silane coupling agent, 3-glycydyloxypropyltrimethoxysilane, GTS, was added to 100 parts by mass of $Sr(OH)_2$ and stirred well with a Henschel mixer. The mixture was dried in air at room temperature for 24 hours to obtain $Sr(OH)_2$ which was surface treated with the silane coupling agent, GTS.

Example 16

259.57 g (1.2 mols) of diphenyl silane diol (DPS) and 189.07 g (0.8 mol) of 3-glycydyloxypropyltrimethoxysilane (GTS) were mixed and heated at 80 degrees C. for 10 minutes with stirring. $Sr(OH)_2$ which was surface treated with the silane coupling agent (GTS) in the Preparation Example 13 was added to the mixture in an amount of $Sr(OH)_2$ of 0.02 mol and, then, heated at 80 degrees C. for 4 hours to react, while removing methanol.

Comparative Example 16

Example 16 was repeated except that $Sr(OH)_2$ which had not be surface treated with a silane coupling agent was used in place of the catalyst used in Example 16.

In Example 16 and Comparative Example 16, a reaction rate and an amount of the remaining catalyst were determined according to the aforesaid manner. The results are as shown in Table 11.

TABLE 11

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 1 hour | 4 hours | ppm |
| Example 16 | $Sr(OH)_2$ | GTS | 0.02 | 1200 | 1130 | 1402 | 80 |
| Com. Ex. 16 | | — | 0.02 | 1800 | 1056 | 1311 | 100 |

Example 17

199.60 g (1.2 mols) of 1,1,3,3-tetramethyldisiloxane-1,3-diol(TDS), 118.59 g (0.8 mol) of trimethoxyvinylsilane (TVS) and 79.55 g (20 wt %) of xylene were mixed and heated at 40 degrees C. for 10 minutes with stirring. $Ba(OH)_2 \cdot 8H_2O$ which was surface treated with the silane coupling agent(TVS) in the Preparation Example 1 was added to the mixture in an amount of $Ba(OH)_2 \cdot 8H_2O$ of 0.02 mol and, then, heated at 40 degrees C. for 1 hour to react.

Example 18

199.60 g (1.2 mols) of 1,1,3,3-tetramethyldisiloxane-1,3-diol(TDS), 118.59 g (0.8 mol) of trimethoxyvinylsilane (TVS) and 79.55 g (20 wt %) of xylene were mixed and heated at 40 degrees C. for 10 minutes with stirring. $Ba(OH)_2$ which was surface treated with the silane coupling agent (TVS) in the Preparation Example 4 was added to the mixture in an amount of $Ba(OH)_2$ of 0.02 mol and, then, heated at 40 degrees C. for 1 hour to react.

Example 19

199.60 g (1.2 mols) of 1,1,3,3-tetramethyldisiloxane-1,3-diol(TDS), 118.59 g (0.8 mol) of trimethoxyvinylsilane (TVS) and 79.55 g (20 wt %) of xylene were mixed and heated at 40 degrees C. for 10 minutes with stirring. $Sr(OH)_2$ which was surface treated with the silane coupling agent (TVS) in the Preparation Example 9 was added to the mixture in an amount of $Sr(OH)_2$ of 0.02 mol and, then, heated at 40 degrees C. for 1 hour to react.

Comparative Example 17

Example 17 was repeated except that $Ba(OH)_2 \cdot 8H_2O$ which had not be surface treated with a silane coupling agent was used in place of the catalyst used in Example 17.

Comparative Example 18

Example 18 was repeated except that $Ba(OH)_2$ which had not be surface treated with a silane coupling agent was used in place of the catalyst used in Example 18.

Comparative Example 19

Example 18 was repeated except that 0.05 mol of $Ba(OH)_2$ which had not be surface treated with a silane coupling agent was used in place of the catalyst used in Example 18.

Comparative Example 20

Example 19 was repeated except that $Sr(OH)_2$ which had not be surface treated with a silane coupling agent was used in place of the catalyst used in Example 19.

In Examples 17-19 and Comparative Examples 17-20, a reaction rate and an amount of the remaining catalyst were determined according to the following manner. The results are as shown in Tables 12 to 14.

[Reaction Rate]

During the reaction, the reaction mixture was observed to record a time when the reaction mixture turned from white turbidity to transparency, which means that all of the DPS monomer, which is solid powder, reacted. Subsequently, the reaction mixture was further aged. Samples of the mixture were taken at the times of 20 minutes and one hour after starting the reaction. The weight average molecular weights (Mw) of the condensates were determined by GPC.

[Amount of the Remaining Catalyst]

After the reaction ended, the solvent was removed and, then, the catalyst was removed by filtration through a filter having pore sizes of 0.95 μm. The polyorganosiloxane obtained was dissolved in the same amount of xylene to prepare a sample solution. Ion-exchanged water was added to the sample solution in an amount of 10 times the weight of the sample solution and shaken to extract the catalyst remaining in the sample solution into water. The water extract was subjected to atomic absorption analysis to determine the amount of the catalyst remaining in the polyorganosiloxane.

TABLE 12

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 20 min. | 1 hour | ppm |
| Example 17 | Ba(OH)$_2$·8H$_2$O | TVS | 0.02 | 88 | 2889 | 8322 | 190 |
| Com. Ex. 17 | — | | 0.02 | 182 | 1687 | 4313 | 250 |

TABLE 13

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 20 min. | 1 hour | ppm |
| Example 18 | Ba(OH)$_2$ | TVS | 0.02 | 194 | 1522 | 3412 | 160 |
| Com. Ex. 18 | — | | 0.02 | 411 | 1269 | 2856 | 210 |
| Com. Ex. 19 | — | | 0.05 | 216 | 1488 | 3251 | 550 |

TABLE 14

| | Catalyst | | Amount of a catalyst, | Reaction time, | Mw, after | Mw, after | Amount of the remaining catalyst, |
|---|---|---|---|---|---|---|---|
| | Compound | Silane coupling agent | mol | sec. | 20 min. | 1 hour | ppm |
| Example 19 | Sr(OH)$_2$ | TVS | 0.02 | 1500 | The reaction did not finish yet. | 1008 | 110 |
| Com. Ex. 20 | — | | 0.02 | 3300 | The reaction did not finish yet. | 634 | 150 |

As seen in Tables 1 to 14, in the conventional manner where the compounds of Group II elements were not surface treated, the reaction rate was slow, as in Comparative Examples 1, 3, 5 to 8, 10, 12 to 13, 15 to 18 and 20. Further, in the method where the compounds of Group II elements were not surface treated, when the amount of the catalyst was increased in order to raise the reaction rate, the amount of the catalyst remaining in the product increased, which is not preferable, as in Comparative Examples 2, 4, 9, 11, 14 and 19. In contrast, in the present method where the compounds of Group II elements was surface treated with a silane coupling agent, the reaction rate is made faster without increasing the amount of the catalyst remaining in the product obtained, as in Examples 1 to 19.

INDUSTRIAL APPLICABILITY

The present method makes a condensation reaction time shorter and provides a desired polyorganosiloxane efficiently in the preparation of polyorganosiloxane which comprises a step of subjecting at least one organic silicon compound having a silanol group and/or an alkoxy silyl group. Further, an amount of impurities remaining in a product obtained in the present method is less and, therefore, is particularly advantageous in fields where precise control on materials, such as the fields of optical materials, electron materials and medical materials.

The invention claimed is:

1. A method for preparing a polyorganosiloxane, the method comprising: a step of subjecting at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms, to a condensation reaction in the presence of a catalyst (C), wherein the catalyst (C) comprises at least one (C1) selected from the group consisting of hydroxides of elements in Group II of the periodic table, hydrates of hydroxides of elements in Group II of the periodic table and oxides of elements in Group II of the periodic table, and a silane coupling agent (C2).

2. The method according to claim 1, wherein an amount of the catalyst (C) is such that an amount of the component (C1) is 0.0001 to 20 mol %, based on a total molar amount of the organic silicon compound subjected to the condensation reaction.

3. The method according to claim 1, wherein said organic silicon compound comprises (A) at least one organic silicon compound having at least one silanol group in the molecule and (B1) at least one organic silicon compound having at least one —OX group bonding to a silicon atom in the molecule, wherein X is a hydrogen atom, an alkyl group having 1 to 10 carbon atoms or an alkoxyalkyl group having 2 to 10 carbon atoms.

4. The method according to claim 1, wherein said organic silicon compound comprises (B2) one or more organic silicon compounds having at least one —OX' group bonding to a silicon atom in the molecule, wherein X' is an alkyl group having 1 to 10 carbon atoms or an alkoxyalkyl group having 2 to 10 carbon atoms.

5. The method according to claim 1, wherein said organic silicon compound comprises one or more organic silicon compounds having at least one silanol group and at least one —OX' group bonding to a silicon atom in the molecule, wherein X' is an alkyl group having 1 to 10 carbon atoms or an alkoxyalkyl group having 2 to 10 carbon atoms.

6. The method according to claim 3, wherein the component (A) is represented by the following general formula (1):

$$(R^1_a SiO_{(4-a-b)/2}(OH)_b)_n \quad (1)$$

wherein $R^1$ is, independently of each other, a hydrogen atom or a monovalent hydrocarbon group having 1 to 18 carbon atoms, and optionally having an oxygen, halogen, nitrogen or sulfur atom, a and b are independent among the parenthesized repeating units, a is an integer of from 0 to 3 and b is an integer of from 0 to 4, provided that the total of a and b is from 0 to 4, and n is an integer of from 1 to 10,000, provided that the organic silicon compound has at least one —OH group bonding to a silicon atom in the molecule, and the component (B1) is represented by the following general formula (2):

$$(R^1_a SiO_{(4-a-b-c)/2}(OH)_b(OR^2)_c)_n \quad (2)$$

wherein $R^1$ is, independently of each other, a hydrogen atom or a monovalent hydrocarbon group having 1 to 18 carbon atoms, and optionally having an oxygen, halogen, nitrogen or sulfur atom, $R^2$ is, independently of each other, an alkyl group having 1 to 10 carbon atoms or an alkoxyalkyl group having 2 to 10 carbon atoms, a, b and c are independent among the parenthesized repeating units, a is an integer of from 0 to 3, b is an integer of from 0 to 4, and c is an integer of from 0 to 4, provided that the total of a, b and c is from 0 to 4, and n is an integer of from 1 to 10,000, provided that the organic silicon compound has at least one —OH group bonding to a silicon atom or —OR² group bonding to a silicon atom in the molecule.

7. The method according to claim 4, wherein the component (B2) is represented by the following general formula (3):

$$(R^1_a SiO_{(4-a-c)/2}(OR^2)_c)_n \quad (3)$$

wherein $R^1$ is, independently of each other, a hydrogen atom or a monovalent hydrocarbon group having 1 to 18 carbon atoms, and optionally having an oxygen, halogen, nitrogen or sulfur atom, $R^2$ is, independently of each other, an alkyl group having 1 to 10 carbon atoms or an alkoxyalkyl group having 2 to 10 carbon atoms, a and c are independent among the parenthesized repeating units, a is an integer of from 0 to 3 and c is an integer of from 0 to 4, provided that the total of a and c is from 0 to 4, and n is an integer of from 1 to 10,000, provided that the organic silicon compound has at least one —OR² group bonding to a silicon atom in the molecule.

8. The method according to claim 5, wherein the organic silicon compound is represented by the following general formula (4):

$$(R^1_a SiO_{(4-a-b-c)/2}(OH)_b(OR^2)_c)_n \quad (4)$$

wherein $R^1$ is, independently of each other, a hydrogen atom or a monovalent hydrocarbon group having 1 to 18 carbon atoms, and optionally having an oxygen, halogen, nitrogen or sulfur atom, $R^2$ is, independently of each other, an alkyl group having 1 to 10 carbon atoms or an alkoxyalkyl group having 2 to 10 carbon atoms, a, b and c are independent among the parenthesized repeating units, a is an integer of from 0 to 3, b is an integer of from 0 to 4, and c is an integer of from 0 to 4, provided that the total of a, b and c is from 0 to 4, and n is an integer of from 1 to 10,000, provided that the organic silicon compound has at least one —OH group bonding to a silicon atom and at least one —OR² group bonding to a silicon atom in the molecule.

9. The method according to claim 1, wherein the condensation reaction is carried out in the presence of (D) at least one solvent.

10. The method according to claim 9, the solvent is at least one selected from the group consisting of water and hydrocarbons, aromatic hydrocarbons, alcohols, alcohol esters, ketons, ethers, esters, hydrocarbon cyanides, amines, amides, halogenated hydrocarbons and sulfur-containing compounds.

11. The method according to claim 1, wherein the catalyst (C) is obtained by a surface treatment, wherein the surface treatment is done before the condensation reaction.

* * * * *